US012770310B2

(12) United States Patent
Tsuyuki

(10) Patent No.: US 12,770,310 B2
(45) Date of Patent: Oct. 20, 2026

(54) PHOTON COUNTING X-RAY COMPUTED TOMOGRAPHY APPARATUS, RECONSTRUCTION PROCESSING APPARATUS, AND NON-VOLATILE COMPUTER-READABLE STORAGE MEDIUM STORING THEREIN PHOTON COUNTING INFORMATION OBTAINING PROGRAM

(71) Applicant: Canon Kabushiki Kaisha, Tokyo (JP)

(72) Inventor: Masaharu Tsuyuki, Nasushiobara (JP)

(73) Assignee: Canon Kabushiki Kaisha, Tokyo (JP)

(*) Notice: Subject to any disclaimer, the term of this patent is extended or adjusted under 35 U.S.C. 154(b) by 415 days.

(21) Appl. No.: 18/326,104

(22) Filed: May 31, 2023

(65) Prior Publication Data

US 2023/0419564 A1 Dec. 28, 2023

(30) Foreign Application Priority Data

Jun. 22, 2022 (JP) ................................. 2022-100050

(51) Int. Cl.
*G06T 12/20* (2026.01)
*A61B 6/00* (2024.01)
(Continued)

(52) U.S. Cl.
CPC .............. *G06T 12/20* (2026.01); *A61B 6/032* (2013.01); *A61B 6/035* (2013.01); *A61B 6/4241* (2013.01);
(Continued)

(58) Field of Classification Search
CPC . G06T 11/006; G06T 11/008; G06T 2210/41; G06T 2211/40; G06T 2211/421;
(Continued)

(56) References Cited

U.S. PATENT DOCUMENTS

2015/0178957 A1* 6/2015 Zou ........................ A61B 6/482
382/131
2015/0198725 A1* 7/2015 Tamura ..................... G01T 1/17
378/5
(Continued)

FOREIGN PATENT DOCUMENTS

JP 2-191438 A 7/1990
JP 2015-528901 A 10/2015
(Continued)

OTHER PUBLICATIONS

Rajendran, Kishore, et al. "First clinical photon-counting detector CT system: technical evaluation." Radiology 303.1 (2022): 130-138. (Year: 2022).*

(Continued)

*Primary Examiner* — Sumati Lefkowitz
*Assistant Examiner* — Ryan P Potts
(74) *Attorney, Agent, or Firm* — Oblon, McClelland, Maier & Neustadt, L.L.P.

(57) ABSTRACT

A photon counting X-ray computed tomography apparatus includes a photon counting detector and a time digital converter. The photon counting detector outputs a pulse corresponding to photons included in an X-ray, and the time digital converter obtains time information corresponding to timing at which the photons were detected, based on the pulse.

8 Claims, 4 Drawing Sheets

(51) Int. Cl.

*A61B 6/03* (2006.01)
*A61B 6/42* (2024.01)
*G01T 1/24* (2006.01)
*G04F 10/00* (2006.01)
*G06T 12/30* (2026.01)

(52) U.S. Cl.

CPC .......... *A61B 6/4266* (2013.01); *A61B 6/5205* (2013.01); *G01T 1/247* (2013.01); *G04F 10/005* (2013.01); *G06T 12/30* (2026.01); *G06T 2210/41* (2013.01); *G06T 2211/40* (2013.01); *G06T 2211/421* (2013.01)

(58) Field of Classification Search

CPC ......... G06T 2207/10081; G06T 7/0012; G06T 11/005; G06T 2207/10116; G06T 2211/408; G06T 2207/30004; G06T 2207/10072; G06T 12/20; G06T 12/00; G06T 12/30; A61B 6/035; A61B 6/4241; A61B 6/4266; A61B 6/032; A61B 6/5205; A61B 6/482; A61B 6/4233; A61B 6/481; A61B 6/5217; A61B 6/4035; A61B 6/5258; A61B 6/03; A61B 6/583; A61B 6/037; A61B 6/025; A61B 6/4208; A61B 6/5282; A61B 6/5264; A61B 2090/3762; A61B 6/54; A61B 6/585; A61B 6/582; A61B 6/42; A61B 6/4429; A61B 6/4078; A61B 6/4085; G01T 1/247; G01T 1/17; G01T 1/36; G01T 1/20; G01T 1/1647; G01T 1/2985; G01T 1/24; G01T 7/005; G01T 1/241; G01T 1/16; G01T 1/18; G01T 1/2018; G04F 10/005; G06V 2201/03; G16H 30/40; G01N 23/046; H10F 39/189; H10F 30/29; H10F 39/195

See application file for complete search history.

(56) References Cited

U.S. PATENT DOCUMENTS

| | | | | |
|---|---|---|---|---|
| 2015/0316663 | A1* | 11/2015 | Herrmann | G01T 1/247 382/132 |
| 2017/0146672 | A1* | 5/2017 | Chen | G01T 1/20182 |
| 2017/0186195 | A1* | 6/2017 | Lin | A61B 6/5258 |
| 2018/0192977 | A1* | 7/2018 | Jin | G01V 5/22 |
| 2021/0113178 | A1* | 4/2021 | Zhou | A61B 6/54 |
| 2021/0369222 | A1* | 12/2021 | Fontaine | A61B 6/5205 |
| 2022/0167936 | A1* | 6/2022 | Sundberg | A61B 6/5294 |
| 2023/0309937 | A1* | 10/2023 | Sossin | G06V 10/774 378/5 |

FOREIGN PATENT DOCUMENTS

| | | | | |
|---|---|---|---|---|
| JP | 2018-110715 A | | 7/2018 | |
| JP | 2019090674 A | * | 6/2019 | |
| WO | WO-2008099314 A2 | * | 8/2008 | G06T 11/005 |

OTHER PUBLICATIONS

Shikhaliev, Polad M., Tong Xu, and Sabee Molloi. “Photon counting computed tomography: concept and initial results.” Medical physics 32.2 (2005): 427-436. (Year: 2005).*

Shikhaliev, Polad M., et al. “Scanning-slit photon counting x-ray imaging system using a microchannel plate detector.” Medical Physics 31.5 (2004): 1061-1071. (Year: 2004).*

Office Action issued Apr. 7, 2026, in corresponding Japanese Patent Application No. 2022-100050, citing document 1 herein, 2 pages.

Office Action issued Aug. 18, 2026, in corresponding Japanese Patent Application No. 2022-100050 with English translation, 7 pages.

* cited by examiner

PHOTON COUNTING X-RAY COMPUTED TOMOGRAPHY APPARATUS, RECONSTRUCTION PROCESSING APPARATUS, AND NON-VOLATILE COMPUTER-READABLE STORAGE MEDIUM STORING THEREIN PHOTON COUNTING INFORMATION OBTAINING PROGRAM

CROSS-REFERENCE TO RELATED APPLICATIONS

This application is based upon and claims the benefit of priority from Japanese Patent Application No. 2022-100050, filed on Jun. 22, 2022, the entire contents of which are incorporated herein by reference.

FIELD

Embodiments described herein relate generally to a photon counting X-ray computed tomography apparatus, a reconstruction processing apparatus, and a non-volatile computer-readable storage medium storing therein a photon counting information obtaining program.

BACKGROUND

Image reconstruction techniques used by conventional X-ray computed tomography apparatuses include a back-projection method. In a backprojection reconstruction, back-projection is carried out on sinogram data by using an X-ray tube focal point representing an integral time period of a corresponding view and positions of detector elements for the view. For this reason, there is a problem where, on the assumption that projection data of the sinogram has a finer positional and/or temporal resolution than the integral time period, a reconstructed image may not reflect the resolution (i.e., the resolution may not be improved).

DETAILED DESCRIPTION

Figure 1:
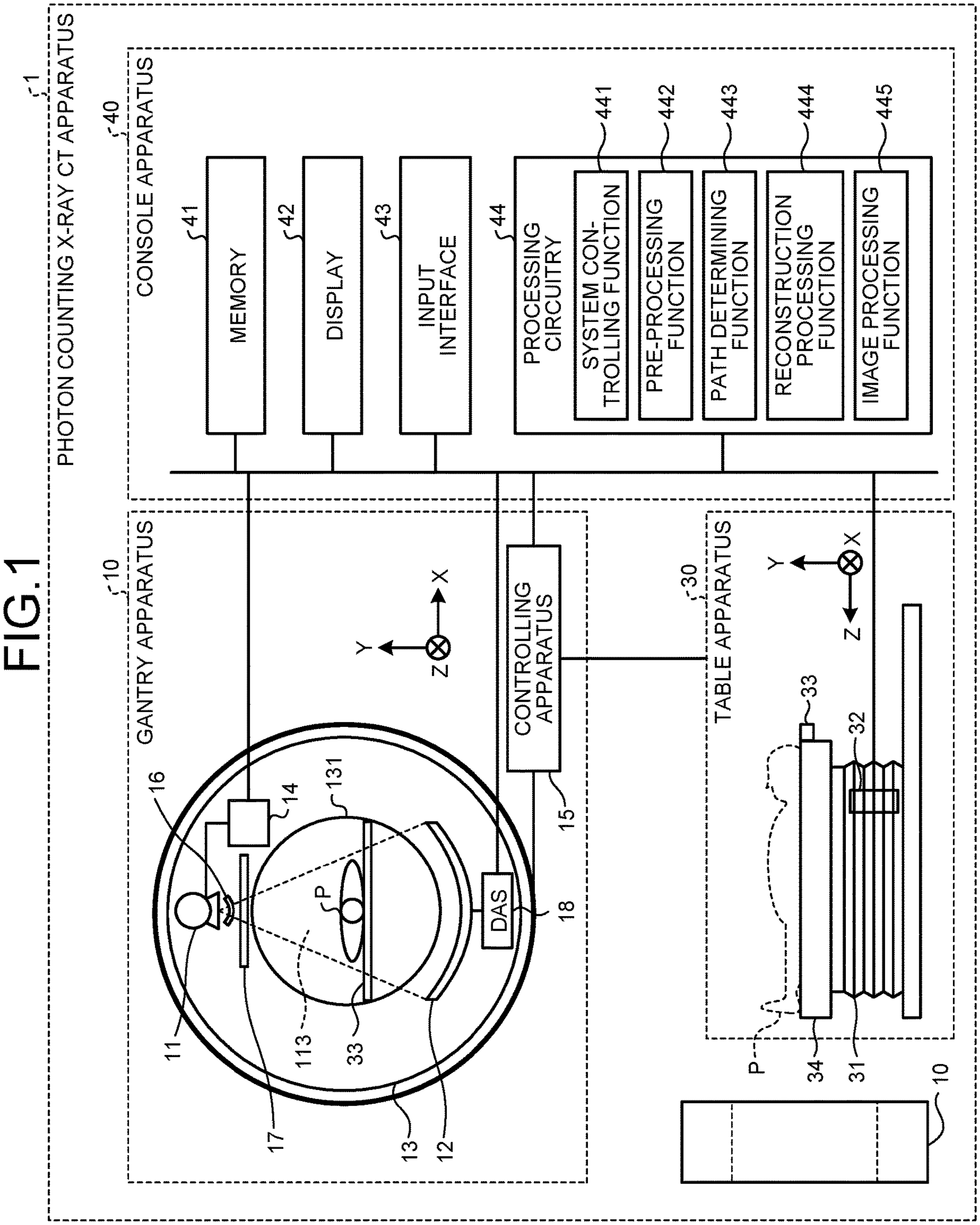
FIG. 1 is a diagram illustrating an exemplary configuration of a photon counting X-ray computed tomography (CT) apparatus according to an embodiment.

A photon counting X-ray computed tomography apparatus according to an embodiment includes a photon counting detector and a time digital converter. The photon counting detector is configured to output a pulse corresponding to photons included in an X-ray; and the time digital converter is configured to obtain time information corresponding to timing at which the photons were detected, on the basis of the pulse.

Exemplary embodiments of a photon counting x-ray computed tomography apparatus, a reconstruction processing apparatus, a photon counting information obtaining method, a reconstruction processing method, a photon counting information obtaining program, and a reconstruction processing program will be explained in detail below, with reference to the accompanying drawings. In the following embodiments, some of the elements that are referred to by using the same reference characters are assumed to perform the same operations, and duplicate explanations thereof will be omitted as appropriate. To explain specific examples, the X-ray computed tomography apparatus according to an embodiment will be explained as an X-ray computed tomography apparatus of a photon counting type (hereinafter, "photon counting X-ray computed tomography (CT) apparatus") capable of carrying out photon counting CT.

The photon counting X-ray CT apparatus is an apparatus capable of reconstructing X-ray CT image data having a high signal-to-noise (S/N) ratio, by employing an X-ray detector based on a photon counting method (hereinafter, "photon counting detector") to count X-rays that have passed through an examined subject (hereinafter, "patient"). In addition to the photon counting detector, the X-ray computed tomography apparatus according to an embodiment may include an integral-type X-ray detector (based on a current mode measuring method).

Embodiments

FIG. 1 is a diagram illustrating an exemplary configuration of a photon counting X-ray CT apparatus 1 according to an embodiment of the present disclosure. As illustrated in FIG. 1, the photon counting X-ray CT apparatus 1 includes a gantry apparatus 10, a table apparatus 30, and a console apparatus 40. In the present embodiment, a rotation axis of a rotating frame 13 in a non-tilt state or the longitudinal direction of a tabletop 33 of the table apparatus 30 is defined as a Z-axis direction; an axial direction orthogonal to the Z-axis direction and parallel to a floor surface is defined as an X-axis direction; and an axial direction orthogonal to the Z-axis direction and perpendicular to the floor surface will be defined as a Y-axis direction. Although FIG. 1 illustrates the gantry apparatus 10 in multiple locations for the sake of convenience in the explanations, the photon counting X-ray CT apparatus 1 in actuality is configured to include the single gantry apparatus 10.

The gantry apparatus 10 and the table apparatus 30 are configured to operate on the basis of an operation received from a user via the console apparatus 40 or an operation received from the user via an operation unit provided for the gantry apparatus 10 or the table apparatus 30. The gantry apparatus 10, the table apparatus 30, and the console apparatus 40 are connected in a wired or wireless manner, so as to be able to communicate with one another.

The gantry apparatus 10 is an apparatus including an imaging system configured to radiate X-rays onto a patient P and to acquire projection data from detection data of X-rays that have passed through the patient P. The gantry apparatus 10 includes an X-ray tube 11 (an X-ray generating unit), a photon counting detector 12, the rotating frame 13, an X-ray high-voltage apparatus 14, a controlling apparatus 15, a bow-tie filter 16, a collimator 17, and a Data Acquisition System (DAS) 18.

The X-ray tube 11 is a vacuum tube configured to generate X-rays by causing thermo electrons to be emitted from a negative pole (a filament) toward a positive pole (a target or an anode), with application of high voltage and a supply of a filament current from the X-ray high-voltage apparatus 14. As a result of the thermo electrons colliding with the target, the X-rays are generated. The X-rays generated at an X-ray tube focal point of the X-ray tube 11 go through an X-ray emission window of the X-ray tube 11 so as to be formed into a cone beam shape via the collimator 17 and emitted onto the patient P. For instance, examples of the X-ray tube 11 include a rotating anode X-ray tube configured to generate the X-rays by having the thermo electrons emitted onto a rotating anode.

The photon counting detector 12 is configured to count photons in the X-rays generated by the X-ray tube 11. For example, the photon counting detector 12 is configured to output a pulse corresponding to the photons included in the X-rays. More specifically, the photon counting detector 12 is configured to detect, in units of photons, the X-rays that were emitted from the X-ray tube 11 and have passed through the patient P and is configured to output an electrical signal corresponding to the amount of the X-rays to the DAS 18. For example, the photon counting detector 12 includes a plurality of columns of detecting elements in each of which a plurality of detecting elements are arranged in a channel direction along an arc while being centered on the focal point of the X-ray tube 11. For example, the photon counting detector 12 has a structure in which the plurality of columns of detecting elements are arranged in a slice direction (a row direction). The photon counting detector 12 may be referred to as a main detector configured to detect the X-rays that have passed through the patient P.

More specifically, the photon counting detector 12 is, for example, an indirect-conversion type detector including a grid, a scintillator array, and an optical sensor array. The scintillator array includes a plurality of scintillators. Each of the scintillators includes a scintillator crystal that outputs light in a photon quantity corresponding to the amount of incident X-rays. The grid is arranged on a surface of the scintillator array that is positioned on the X-ray incident side and includes an X-ray blocking plate having a function of absorbing scattered X-rays. The optical sensor array includes a plurality of optical sensor groups. Each of the optical sensor groups includes a plurality of optical sensors.

Each of the plurality of optical sensors has a function of amplifying the received light from a corresponding one of the scintillators and converting the amplified light into an electrical signal. The optical sensors may be, for example, Avalanche Photo-Diodes (APDs) or Silicon Photo Multipliers (SiPMs). In other words, the optical sensors are configured to receive the light coming from the scintillators and to output electrical signals (pulses) corresponding to the incident X-ray photons. In other words, each of the plurality of optical sensors is configured to output a pulse corresponding to the photons included in the corresponding X-rays. The plurality of optical sensors correspond to the plurality of detecting elements. In other words, the photon counting detector 12 includes the plurality of detecting elements.

In this situation, the electrical signal output by each of the detecting elements may be referred to as a detection signal. A crest value (voltage) of the electrical signal (the pulse) has a correlation with an energy value of the X-ray photons. Alternatively, the photon counting detector 12 may be a direct-conversion type detector including a semiconductor element configured to convert the incident X-rays into electrical signals. When the photon counting detector 12 is a direct-conversion type detector, a plurality of electrodes in the semiconductor element correspond to the plurality of detecting elements.

The rotating frame 13 is configured to support the X-ray tube 11 and the photon counting detector 12 so as to be rotatable on the rotation axis. More specifically, the rotating frame 13 is an annular frame configured to support the X-ray tube 11 and the photon counting detector 12 so as to oppose each other and configured to rotate the X-ray tube 11 and the photon counting detector 12 via the controlling apparatus 15 (explained later). The rotating frame 13 is rotatably supported by a fixed frame formed by using metal such as aluminum. More specifically, the rotating frame 13 is connected to an edge part of the fixed frame via a bearing. The rotating frame 13 is configured to rotate on a rotation axis Z at a constant angular speed, by receiving motive power from a driving mechanism of the controlling apparatus 15.

In addition to the X-ray tube 11 and the photon counting detector 12, the rotating frame 13 further includes and supports the X-ray high-voltage apparatus 14 and the DAS 18. The rotating frame 13 configured in this manner is housed in a casing which has a substantially circular cylindrical shape and in which an opening (a bore) 131 serving as an imaging space is formed. The opening 131 substantially matches a Field of View (FOV). The central axis of the opening 131 matches the rotation axis Z of the rotating frame 13. In this situation, the detection data generated by the DAS 18 is, for example, transmitted through optical communication from a transmitter including a light emitting diode (LED), to a receiver including a photodiode and being provided in a non-rotating part (e.g., the fixed frame) of the gantry apparatus 10, and is further transferred to the console apparatus 40. In this situation, the method for transmitting the detection data from the rotating frame 13 to the non-rotating part of the gantry apparatus 10 is not limited to the abovementioned optical communication, and it is acceptable to adopt any of contactless data transfer methods.

The X-ray high-voltage apparatus 14 includes: a high-voltage generating apparatus including electrical circuitry such as a transformer, a rectifier, and the like and having a function of generating the high voltage to be applied to the X-ray tube 11 and the filament current to be supplied to the X-ray tube 11; and an X-ray controlling apparatus configured to control output voltage corresponding to the X-rays to be emitted by the X-ray tube 11. The high-voltage generating apparatus may be of a transformer type or an inverter type. Further, the X-ray high-voltage apparatus 14 may be provided for the rotating frame 13 or may be provided so as to belong to the fixed frame (not illustrated) of the gantry apparatus 10.

The controlling apparatus 15 includes processing circuitry having a Central Processing Unit (CPU) or the like and a driving mechanism such as a motor and an actuator or the like. As hardware resources thereof, the processing circuitry includes a processor such as the CPU or a Micro Processing Unit (MPU) and one or more memory elements such as a Read-Only Memory (ROM), a Random Access Memory (RAM), and/or the like. Alternatively, the controlling apparatus 15 may be realized by using an Application Specific Integrated Circuit (ASIC), a Field Programmable Gate Array (FPGA), or one or more other mechanisms such as a Complex Programmable Logic Device (CPLD) or a Simple Programmable Logic Devices (SPLD). According to a command from the console apparatus 40, the controlling apparatus 15 is configured to control the X-ray high-voltage apparatus 14, the DAS 18, and the like. The processor is configured to realize the abovementioned control by reading and executing programs saved in a memory element.

Further, the controlling apparatus 15 has a function of receiving input signals from an input interface attached to the console apparatus 40 or the gantry apparatus 10 and controlling operations of the gantry apparatus 10 and the table apparatus 30. For example, upon receipt of the input signals, the controlling apparatus 15 is configured to exercise control to rotate the rotating frame 13, control to tilt the gantry apparatus 10, and control to bring the table apparatus 30 and the tabletop 33 into operation. In this situation, the control to tilt the gantry apparatus 10 may be realized as a result of the controlling apparatus 15 rotating the rotating frame 13 on an axis parallel to the X-axis direction, according to an inclination angle (a tilt angle) input through an input interface attached to the gantry apparatus 10.

Further, the controlling apparatus 15 may be provided for the gantry apparatus 10 or for the console apparatus 40. Alternatively, instead of having the programs saved in the memory, the controlling apparatus 15 may be configured to directly incorporate the programs in the circuitry of the processor thereof. In that situation, the processor is configured to realize the abovementioned control by reading and executing the programs incorporated in the circuitry.

The bow-tie filter 16 is disposed on the front surface of an X-ray emission window of the X-ray tube 11. The bow-tie filter 16 is a filter for adjusting the radiation amount of the X-rays emitted from the X-ray tube 11. More specifically, the bow-tie filter 16 is a filter configured to pass and attenuate the X-rays emitted from the X-ray tube 11 so that the X-rays emitted from the X-ray tube 11 onto the patient P has a predetermined distribution. The bow-tie filter 16 is a filter obtained by processing aluminum so as to have a predetermined target angle and a predetermined thickness.

The collimator 17 is configured by using lead plates or the like for narrowing down the X-rays that have passed through the bow-tie filter 16 into an X-ray emission range 113 and is configured to form a slit with a combination of the plurality of lead plates or the like.

Figure 2:
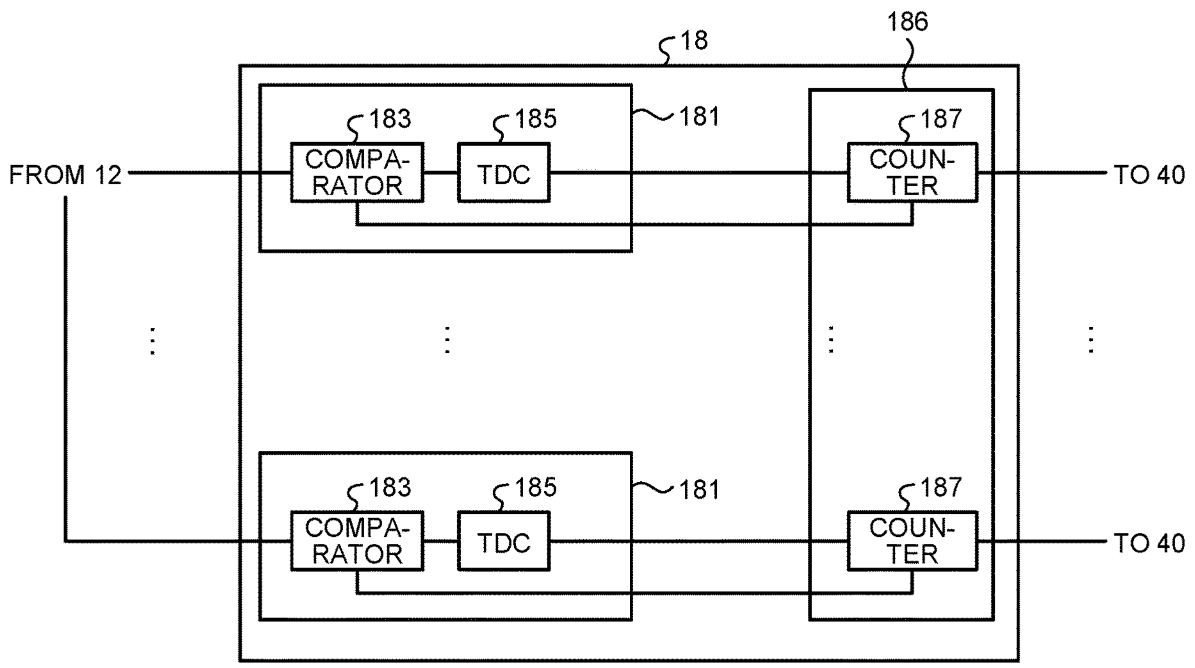
FIG. 2 is a diagram illustrating an example of a configuration of a Data Acquisition System (DAS) according to the embodiment.

FIG. 2 is a diagram illustrating an example of a configuration of the DAS 18. As illustrated in FIG. 2, for example, the DAS 18 includes a plurality of pieces of counting circuitry 181 corresponding to the plurality of detecting elements and a counting unit 186. Each of the plurality of pieces of counting circuitry 181 includes, for example, a comparator 183, and a time digital converter (hereinafter, "TDC") 185. In this situation, each of the plurality of pieces of counting circuitry 181 may electrically be connected to a predetermined number of detecting elements among the plurality of detecting elements.

The comparator 183 is configured to compare a detection signal output from a corresponding detecting element with a plurality of threshold values. In this situation, the detection signal may be amplified by an amplifier provided at a stage preceding the comparator 183. The comparator 183 is connected to threshold value output circuitry configured to output a plurality of threshold value signals corresponding to the plurality of threshold values. The comparator 183 is configured to compare the detection signal with the plurality of threshold values and to output a signal corresponding to a crest value of the detection signal to the console apparatus 40. The comparator 183 may be referred to as a crest discriminator. Because it is possible to apply existing techniques to processing performed by the comparator 183, explanations thereof will be omitted.

The TDC 185 is connected to a system clock configured to output a clock signal. The TDC 185 is configured to output a time at which the detection signal intersects a minimum threshold value of the comparator 183, to the console apparatus 40 as a digital signal. In other words, the TDC 185 is configured to output a photon detection time to the console apparatus 40. Thus, the TDC 185 has obtained time information corresponding to timing at which the photons were detected.

Figure 3:
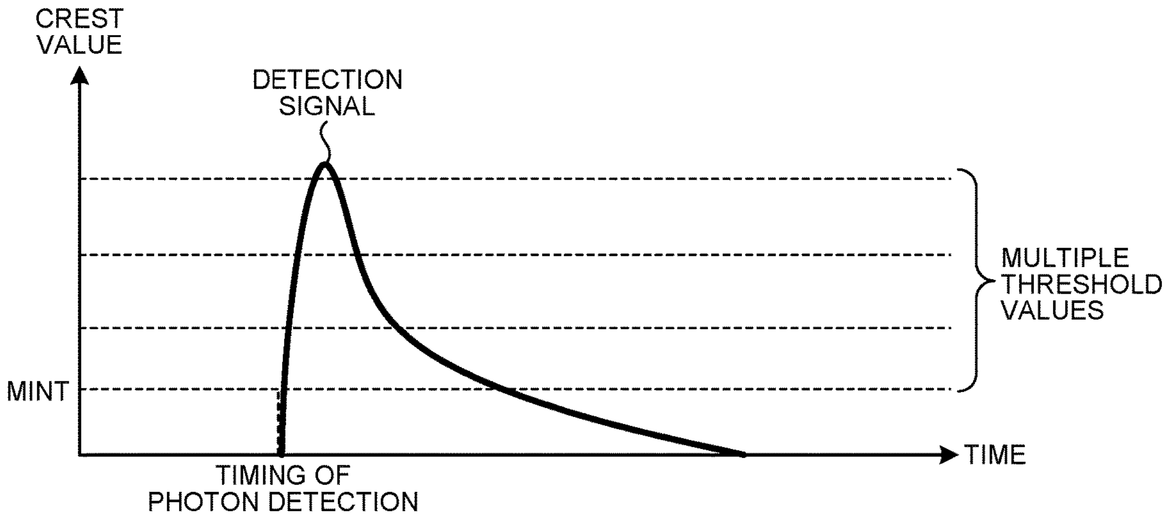
FIG. 3 is a chart according to the embodiment illustrating an example of photon detection timing with respect to a detection signal.

FIG. 3 is a chart illustrating an example of photon detection timing with respect to the detection signal. As illustrated in FIG. 3, the TDC 185 is configured to obtain a point in time at which the detection signal intersects a minimum threshold value MINT, as the time information indicating the photon detection timing. In other words, the TDC 185 is configured to obtain the time information corresponding to the timing at which the photons were detected, on the basis of the pulse output from a corresponding optical sensor. Because it is possible to apply known time digital conversion circuitry to the TDC 185, explanations thereof will be omitted. The TDC 185 corresponds to a time information obtaining unit. Further, functions realized by the processes at the TDC 185 and thereafter may be realized by processing circuitry 44. For example, processing related to the TDC 185 may be realized as a time information obtaining function of the processing circuitry 44, for example.

The counting unit 186 includes a plurality of counters 187 corresponding to the plurality of comparators 183. Each of the plurality of counters 187 is configured to perform a counting process, on the basis of an output from a corresponding one of the comparators 183 and a corresponding one of the TDC 185. For example, the counting unit 186 is configured to perform a photon counting process, by using a detection signal from the photon counting detector 12, together with the time information. Accordingly, the counting unit 186 is configured to generate detection data, which is a result of the photon counting process. The detection data is data in which the quantity of photons in the X-rays with respect to each energy bin is assigned together with the time information. For example, the DAS 18 is configured to count the photons derived from the X-rays (X-ray photons) that were emitted from the X-ray tube 11 and have passed through the patient P and to discriminate energy levels of the counted photons, so as to obtain a result of the counting process. For example, each of the plurality of counters 187 is realized by corresponding counting circuitry 181, as a hardware configuration.

The detection data generated by the DAS 18 is transferred to the console apparatus 40. In this situation, the detection data may be a set of data indicating a channel number, a column number, and a view number (a number expressing the rotation angle of the X-ray tube 11; e.g., 1 to 1,000) identifying the acquired view (which may be called "projection angle") of a detector pixel from which the detection signal based on the time information was generated, as well as the quantity of the photons (the quantity of the counted photons) corresponding to each energy level. In that situation, the channel number, the column number, the view number and the like correspond to position information of the detecting element related to the detected photons. Further, the position information may be calculated from the time information. In an example, an acquisition time at which the view was acquired may be used as the view number. For example, each of the plurality of pieces of counting circuitry 181 in the DAS 18 is realized by a group of circuitry installed with circuitry elements capable of generating the detection data. For example, the detection data corresponds to list data in which the abovementioned items are presented in a list format.

The table apparatus 30 is an apparatus on which the patient P to be scanned is placed and moved and includes a base 31, a table driving apparatus 32, the tabletop 33, and a tabletop supporting frame 34. The base 31 is a casing configured to support the tabletop supporting frame 34 so as to be movable vertically. The table driving apparatus 32 is a motor or an actuator configured to move the tabletop 33 over which the patient P is placed in the longitudinal direction of the tabletop 33. The table driving apparatus 32 is configured to move the tabletop 33, according to control exercised by the console apparatus 40 or control exercised by the controlling apparatus 15. The tabletop 33 provided on the top face of the tabletop supporting frame 34 is a board on which the patient P is placed. Further, in addition to the tabletop 33, the table driving apparatus 32 may be configured to move the tabletop supporting frame 34 in the longitudinal direction of the tabletop 33.

The console apparatus 40 includes a memory 41 (a storage unit), a display 42 (a display unit), an input interface 43 (an input unit), and the processing circuitry 44 (a processing unit). Data communication among the memory 41, the display 42, the input interface 43, and the processing circuitry 44 is performed via a bus.

The memory 41 is a storage apparatus such as a Hard Disk Drive (HDD), a Solid State Drive (SSD), or an integrated circuitry storage apparatus, configured to store therein various types of information. For example, the memory 41 is configured to store therein projection data and reconstructed image data. Instead of being an HDD or an SSD, the memory 41 may be a drive apparatus configured to read and write various types of information from and to a portable storage medium such as a Compact Disc (CD), a Digital Versatile Disc (DVD), or a flash memory, or a semiconductor memory element such as a Random Access Memory (RAM). Further, a save region of the memory 41 may be in the photon counting X-ray CT apparatus 1 or may be in an external storage apparatus connected via a network.

The memory 41 has stored therein various types of programs related to the present embodiment. For example, the memory 41 has stored therein programs related to execution of functions such as a system controlling function 441, a pre-processing function 442, a path determining function 443, a reconstruction processing function 444, and an image processing function 445 which are executed by the processing circuitry 44. Further, the memory 41 is configured to store therein an X-ray path determined by the path determining function 443 so as to be kept in correspondence with the detection data with respect to each view and each detecting element.

The display 42 is configured to display various types of information. For example, the display 42 is configured to output a medical image (a CT image) generated by the processing circuitry 44, a Graphical User Interface (GUI) used for receiving various types of operations from the user, and the like. As the display 42, it is possible to use, for example, a Liquid Crystal Display (LCD), a Cathode Ray Tube (CRT) display, an Organic Electroluminescence Display (OELD), a plasma display, or any of other arbitrary displays, as appropriate. Further, the display 42 may be provided for the gantry apparatus 10. Also, the display 42 may be of a desktop type or may be configured by using a tablet terminal or the like capable of wirelessly communicating with the console apparatus 40 main body. The display 42 corresponds to a display unit.

The input interface 43 is configured to receive various types of input operations from the user, to convert the received input operations into electrical signals, and to output the electrical signals to the processing circuitry 44. For example, the input interface 43 is configured to receive, from the user, an acquisition condition used at the time of acquiring the projection data, a reconstruction condition used at the time of reconstructing the CT image, an image processing condition used at the time of generating a post-processing image from the CT image, and the like. As the input interface 43, it is possible to use, for example, a mouse, a keyboard, a trackball, a switch, a button, a joystick, a touchpad, a touch panel display, and/or the like, as appropriate.

In the present embodiment, the input interface 43 does not necessarily have to include physical operational component parts such as the mouse, the keyboard, the trackball, the switch, the button, the joystick, the touchpad, the touch panel display, and/or the like. For instance, possible examples of the input interface 43 include electrical signal processing circuitry configured to receive an electrical signal corresponding to an input operation from an external input mechanism provided separately from the apparatus and to output the electrical signal to the processing circuitry 44. Further, the input interface 43 is an example of an input unit. In another example, the input interface 43 may be provided for the gantry apparatus 10. Alternatively, the input interface 43 may be configured by using a tablet terminal or the like capable of wirelessly communicating with the console apparatus 40 main body. The input interface 43 corresponds to an input unit.

The processing circuitry 44 is configured to control operations of the entirety of the photon counting X-ray CT apparatus 1 in accordance with the electrical signals of the input operations output from the input interface 43. For example, the processing circuitry 44 includes, as hardware resources thereof, a processor such as a CPU, an MPU, or a Graphics Processing Unit (GPU) and one or more memory elements such as a ROM, a RAM, and/or the like. By employing the processor that executes the programs loaded into any of the memory elements, the processing circuitry 44 is configured to execute the system controlling function 441, the pre-processing function 442, the path determining function 443, the reconstruction processing function 444, and the image processing function 445.

The processing circuitry 44 realizing the system controlling function 441, the pre-processing function 442, the path determining function 443, the reconstruction processing function 444, and the image processing function 445 corresponds to a system controlling unit, a pre-processing unit, a path determining unit, a reconstruction processing unit, and an image processing unit, respectively. The functions 441 to 445 do not necessarily have to be realized by the single piece of processing circuitry. It is also acceptable to structure processing circuitry by combining together a plurality of independent processors, so that the functions 441 to 445 are realized as a result of the processors executing the programs.

The system controlling function 441 is configured to control the functions of the processing circuitry 44 on the basis of the input operations received from the user via the input interface 43. More specifically, the system controlling function 441 is configured to read a control program stored in the memory 41, to load the read program into any of the memory elements in the processing circuitry 44, and to control functional units of the photon counting X-ray CT apparatus 1 according to the loaded control program. For example, the system controlling function 441 is configured to control the functions of the processing circuitry 44 on the basis of the input operations received from the user via the input interface 43.

The pre-processing function 442 is configured to generate data obtained by performing pre-processing processes such as a logarithmic conversion process, an offset correction process, an inter-channel sensitivity correction process, a beam hardening correction, and/or the like, on the detection data output from the DAS 18. The data prior to the pre-processing processes may be referred to as raw data, whereas the data after the pre-processing processes may be referred to as projection data.

The path determining function 443 is configured to identify a detecting element related to the detection of the photons, on the basis of the time information appended to the detection data. Subsequently, on the basis of the time information, the path determining function 443 is configured to identify an X-ray tube focal point for the view related to the identified detecting element. After that, the path determining function 443 is configured to determine an X-ray path related to the detection of the photons, by connecting the identified detecting element to the identified X-ray tube focal point. However, possible X-ray path determining processes are not limited to the procedure described above. For example, the path determining function 443 may be configured to determine an X-ray path related to the detection of the photons, on the basis of the rotation angle of the rotating frame 13 at a detection time of the photons serving as the time information, the position of the X-ray tube focal point on the rotating frame 13, and the position of the detecting element related to the detection time.

Figure 4:
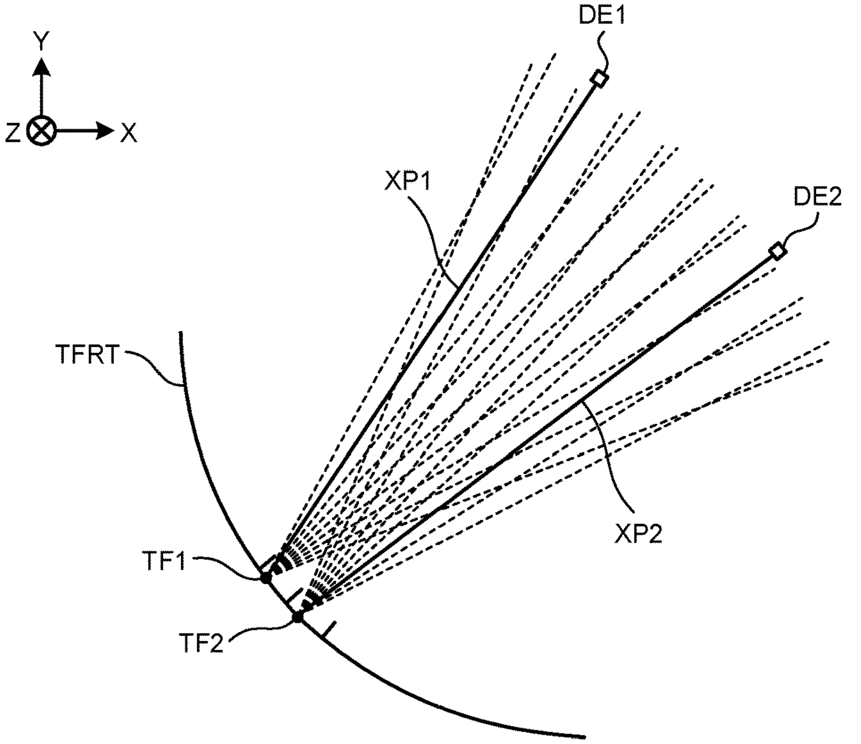
FIG. 4 is a drawing according to the embodiment illustrating examples of determined X-ray paths.

FIG. 4 is a drawing illustrating examples of the determined X-ray paths. As the rotating frame 13 rotates, the X-ray tube focal point illustrated in FIG. 4 moves along a circular track TFRT. As illustrated in FIG. 4, when the photons in an X-ray generated at an X-ray tube focal point TF1 are detected by a detecting element DE1, the path determining function 443 determines a solid line XP1 as an X-ray path corresponding to the detection of the photons. As another example, when the photons in another X-ray generated at an X-ray tube focal point TF2 are detected by a detecting element DE2, the path determining function 443 determines a solid line XP2 as an X-ray path corresponding to the detection of the photons.

On the basis of the time information, the reconstruction processing function 444 is configured to perform a reconstructing process using the X-ray path corresponding to the photons. More specifically, the reconstruction processing function 444 is configured to generate CT image data by performing the reconstructing process that uses a Filtered Back Projection (FBP) method or a successive approximation method, on the projection data generated by the pre-processing function 442. The reconstruction processing function 444 is configured to store the reconstructed CT image data into the memory 41. The projection data generated from a counting result obtained in a photon counting process CT includes information about X-ray energy attenuated due to having passed through the patient P. For this reason, the reconstruction processing function 444 is able to reconstruct X-ray CT image data corresponding to a specific energy component, for example. Further, the reconstruction processing function 444 is able to reconstruct X-ray CT image data corresponding to each of a plurality of energy components, for example.

For instance, when a backprojection method is used in the reconstructing process, the reconstruction processing function 444 is configured, prior to the reconstructing process, to shift (translate) a reconstruction mathematical function (hereinafter, "reconstruction function" which may be referred to as a "reconstruction filter") in accordance with the position of each of the plurality of detecting elements. Usually, a process of convoluting the reconstruction function into the detection data is performed before the reconstructing process. In the following sections, shifting of the reconstruction function will be explained. The detection data is expressed as a pulse waveform having a crest value corresponding to the energy of the detected photons, with respect to each of the detecting elements that detected the photons.

In other words, in FIG. 3 for example, the pulse waveform is expressed with crest values corresponding to energy levels of the photons with respect to time. In contrast, in FIG. 6 (explained later), the pulse waveform expresses impulse corresponding to a channel (the detecting element number) that detected the photons, while the crest value of the impulse has an aligned value that is not dependent on the energy. In other words, because a single photon has the same weight at the time of the reconstruction, the crest value of the impulse exhibits an equal value. For this reason, substantially, in a result of the convolution of the reconstruction function into the detection data, which is carried out prior to the reconstruction, the position of the detecting element that detected the photons serves as an apex of the reconstruction function, while the apex of the reconstruction function is expressed as a crest. In this situation, the crest corresponds to the output from a detecting element and, for example, corresponds to the quantity of the photons detected by each of the plurality of detecting elements. Further, although the reconstruction function is used for reducing out-of-focus phenomena that may be caused by the backprojection method, it is also acceptable to further incorporate an image quality adjustment filter corresponding to an imaged site of the patient P.

As explained above, the reconstruction processing function 444 is configured, prior to the reconstructing process, to shift the reconstruction function in accordance with the position of each of the plurality of detecting elements related to the projection data resulting from the pre-processing and to further generate the reconstruction-purpose projection data by adjusting the crest in accordance with the quantities of the photons. For example, when plurality of photons have simultaneously entered a detecting element (i.e., one detection channel), the reconstruction processing function 444 adjusts the crest. Further, when a photon has entered each of a plurality of detection channels with the same timing as each other, the reconstruction processing function 444 is configured to shift the position without changing the respective crests. The reconstruction function may be stored in the memory 41 as a correspondence table (a Look Up Table (LUT)) corresponding to the crests. In that situation, the reconstruction processing function 444 is configured to compare a data value in the projection data resulting from the pre-processing with the correspondence table and to read a reconstruction function corresponding to the data value from the memory 41. Subsequently, the reconstruction processing function 444 is configured to generate the reconstruction-purpose projection data, by shifting the read reconstruction function in accordance with the position of each of the plurality of detecting elements related to the projection data resulting from the pre-processing. The reconstruction processing function 444 is configured to reconstruct X-ray CT image data by performing the backprojection that uses the path determined with respect to each of the plurality of detecting elements, on the reconstruction function that has been shifted and of which the crest has been adjusted.

Alternatively, as a reconstructing process, the reconstruction processing function 444 may carry out a successive approximation reconstruction based on forward projection and backward projection (backprojection) that use the determined paths. For example, the reconstruction processing function 444 may reconstruct X-ray CT image data by repeatedly performing the forward projection and the backward projection (backprojection) while using the path determined with respect to each of the detecting elements. In that situation, as a sinogram, a reconstruction function that has been shifted and of which the crest has been adjusted may be applied.

For example, according to an instruction received from the user via the input interface 43, the image processing function 445 is configured to perform various types of image processing processes on the reconstructed X-ray CT image data (volume data). Because it is possible to apply any of known processes to the image processing processes as appropriate, explanations thereof will be omitted.

Figure 5:
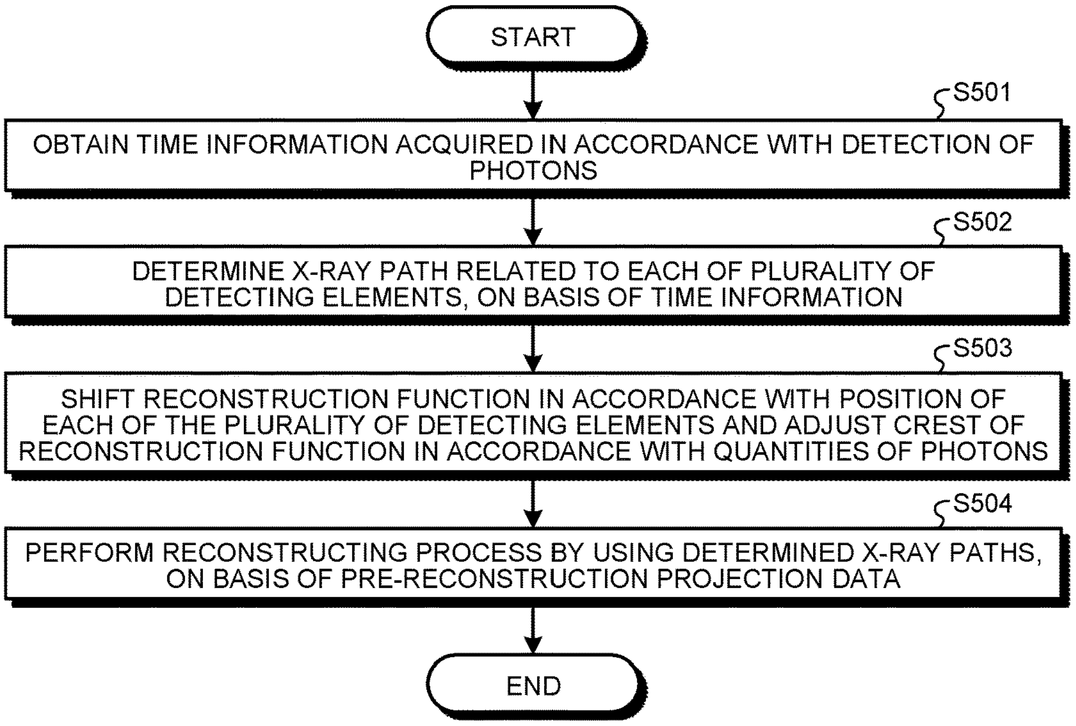
FIG. 5 is a flowchart illustrating an example of a procedure in a reconstructing process according to the embodiment.

A configuration of the photon counting X-ray CT apparatus 1 according to the embodiment has thus been explained. Next, a procedure in the reconstructing process performed by the photon counting X-ray CT apparatus 1 will be explained, with reference to FIG. 5. FIG. 5 is a flowchart illustrating an example of the procedure in the reconstructing process. Before the reconstructing process is performed, the TDC 185 acquires the time information in accordance with the detection of the photons.

Reconstructing Process

Step S501:

The reconstruction processing function 444 obtains the time information acquired by the TDC 185. In an example, when the reconstructing process is carried out by one of various types of servers such as a reconstruction processing apparatus, the reconstruction processing apparatus obtains the time information from the photon counting X-ray CT apparatus 1 together with the detection data. In that situation, the reconstruction processing apparatus stores the time information together with the detection data, into a memory installed therein.

Step S502:

On the basis of the time information, the path determining function 443 determines an X-ray path related to each of the plurality of detecting elements. The path determining function 443 stores the determined paths into the memory 41 so as to be kept in correspondence with the detecting elements and the views in the detection data.

Step S503:

The reconstruction processing function 444 shifts the reconstruction function in accordance with the position of each of the plurality of detecting elements. Additionally, in accordance with the quantities of the photons, the reconstruction processing function 444 adjusts the crest of the reconstruction function. In this manner, the reconstruction processing function 444 generates the pre-reconstruction projection data.

Step S504:

On the basis of the pre-reconstruction projection data, the reconstruction processing function 444 performs a reconstructing process by using the determined X-ray paths. In this manner, the reconstruction processing function 444 performs the reconstructing process by using the accurate paths. Thus, the reconstructing process ends.

The photon counting X-ray CT apparatus 1 according to the embodiment described above is configured to output the pulse corresponding to the photons included in the X-rays and to obtain the time information corresponding to the timing at which the photons were detected, on the basis of the pulse. Further, the photon counting X-ray CT apparatus 1 according to the embodiment is configured to perform the reconstructing process that uses the X-ray paths corresponding to the detected photons, on a basis of the time information. For example, as the reconstructing process, the photon counting X-ray CT apparatus 1 according to the embodiment is configured to perform the successive approximation reconstruction based on the forward projection and the backward projection (backprojection) using the determined paths. Further, the photon counting X-ray CT apparatus 1 according to the embodiment is configured to use the backprojection method for the reconstructing process and is configured, prior to implementing the backprojection method, to shift the reconstruction function in accordance with the position of each of the plurality of detecting elements, and to carry out the backprojection using the determined paths on the shifted reconstruction function.

Consequently, on the basis of the high-precision position information (the X-ray tube focal point and the positions of the detecting elements) included in the detection data in the list format, the photon counting X-ray CT apparatus 1 according to the embodiment is able to perform the reconstructing process by using the X-ray paths corresponding to the detected photons. As a result, the photon counting X-ray CT apparatus 1 according to the embodiment is able to generate X-ray CT image data having an enhanced resolution.

In addition, without the need to perform a convolution calculation of the reconstruction function, the photon counting X-ray CT apparatus 1 according to the embodiment is capable of generating the pre-reconstruction projection data, by using the reconstruction function and the detection data. In the following sections, while using FIG. 6 as an example, the process of generating the pre-reconstruction projection data by using the reconstruction function and the detection data, without performing the convolution calculation of the reconstruction function will be explained.

Figure 6:
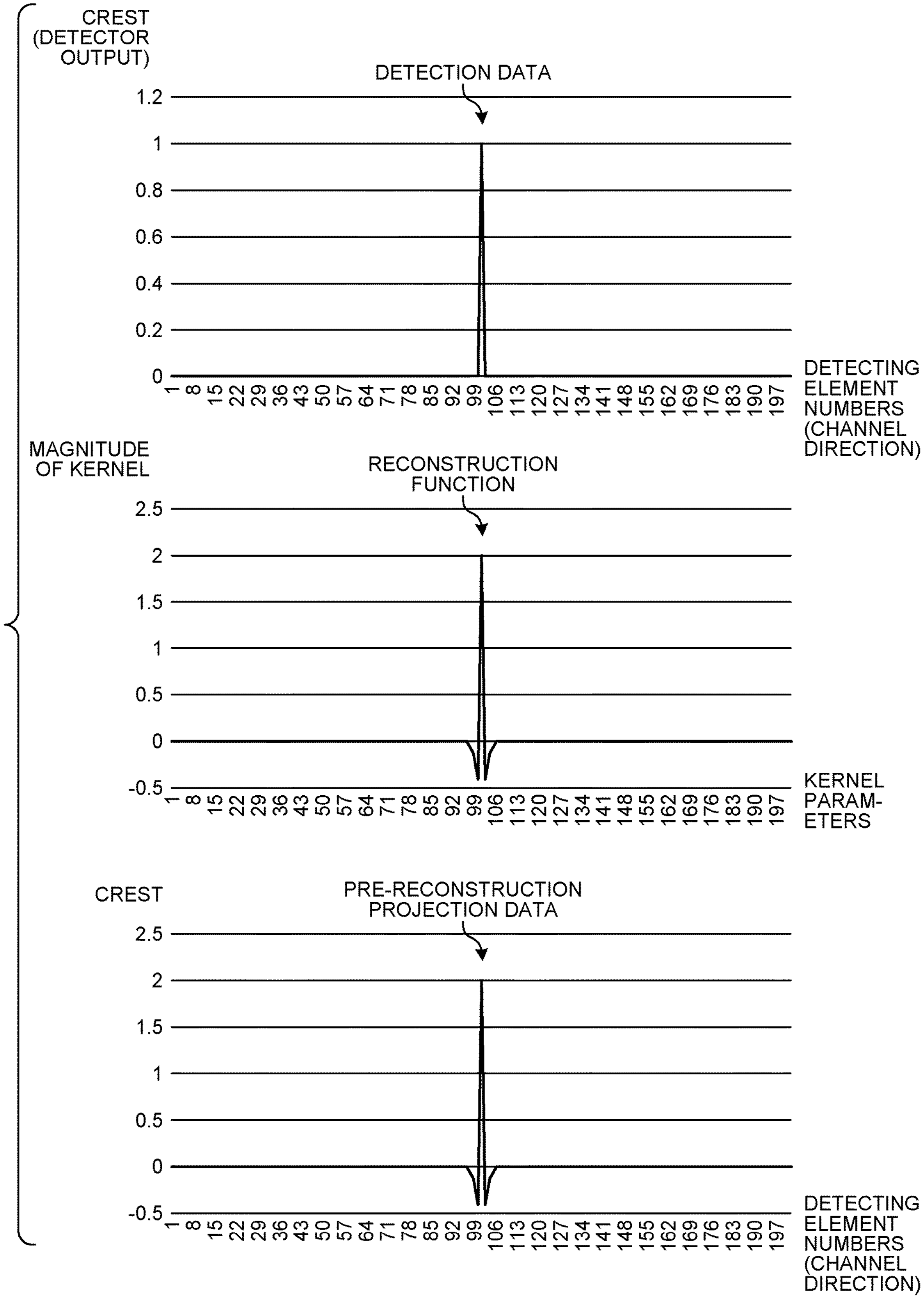
FIG. 6 presents charts illustrating examples of application of a reconstruction mathematical function according to the embodiment.

FIG. 6 presents charts illustrating examples of application of the reconstruction function. As illustrated in FIG. 6, the detection data exhibits delta-function impulse with respect to a number identifying the detecting element that detected photons (hereinafter, "photon detecting element number"). For this reason, a result (the pre-reconstruction projection data) of a convolution calculation on the reconstruction function and the detection data would substantially be equivalent to a result of shifting the position of an apex of a reconstruction function (which may be referred to as "reconstruction kernel"), in accordance with the photon detecting element number. For this reason, the photon counting X-ray CT apparatus 1 according to the present embodiment is able to generate the pre-reconstruction projection data without performing the convolution calculation, by shifting the reconstruction function in accordance with the photon detecting element number and adjusting (stretching and enlarging) the magnitude of the apex of the reconstruction function in accordance with the quantities of the photons. Consequently, the photon counting X-ray CT apparatus 1 according to the embodiment is able to significantly shorten processing time related to the reconstructing process, i.e., to increase the speed of the reconstructing process.

It is therefore possible to improve efficiency of the medical examination (a throughput of the examination) for the patient P.

First Application Example

In the present application example, occurrence of artifacts is reduced in the reconstructing process using the time information corresponding to the detection of the photons. Because the time information corresponds to the detection of the photons, the time information has a higher temporal resolution than in conventional examples. For this reason, there is a possibility that the pre-reconstruction projection data (the sinogram) may have unevenness in data density. The unevenness in the data density may be a cause of a shower artifact or a streak artifact in reconstructed X-ray CT image data. The present application example aims to generate X-ray CT image data in which the occurrence of artifacts such as a shower artifact and/or a streak artifact is reduced.

The reconstruction processing function 444 is configured to integrate pulse quantity values indicating how many pulses were output from each of the plurality of detecting elements over a prescribed time period. The prescribed time period is approximately 10 to 100 times as long as the temporal resolution of the photon detection and is shorter than an integral time period of X-ray detection in a regular integral-type X-ray CT apparatus.

The path determining function 443 is configured to determine an X-ray path with respect to each of the plurality of views and each of the plurality of detecting elements, by calculating an average of a plurality of paths over the prescribed time period, with respect to each of the plurality of views and each of the plurality of detecting elements. Alternatively, the path determining function 443 may be configured to determine X-ray paths to be used in the reconstructing process, by calculating a weighted average while using the quantities of the photons related to the plurality of paths over the prescribed time period as weights.

The reconstruction processing function 444 is configured to perform the reconstructing process on the basis of the integrated quantity value and the average of the plurality of paths over the prescribed time period. Differences from the embodiment lie in that the quantity of the photons used in the reconstructing process is the integrated value over the prescribed time period and that the X-ray path is an average value of the plurality of paths over the prescribed time period. Because the other processes in the reconstructing process are the same as those in the embodiment, explanations thereof will be omitted.

The photon counting X-ray CT apparatus 1 according to the first application example of the embodiment described above is configured, by using the time information, to integrate the pulse quantity values indicating how many pulses were output from each of the plurality of detecting elements over the prescribed time period and to further perform the reconstructing process on the basis of the integrated quantity value and the average of the plurality of paths over the prescribed time period. With this configuration, the photon counting X-ray CT apparatus 1 according to the first application example is able to reduce missing data in the pre-reconstruction projection data (the sinogram). Consequently, the photon counting X-ray CT apparatus 1 according to the first application example is able to generate X-ray CT image data which has a high resolution and in which the occurrence of artifacts such as a shower artifact and/or a streak artifact is reduced (inhibited). Because the other advantageous effects are the same as those of the embodiment, explanations thereof will be omitted.

Second Application Example

In the present application example, an image of a region exhibiting artifacts within the X-ray CT image data (hereinafter, "first reconstructed image") generated from the reconstructing process is replaced with a partial image in the same position as the region within a second reconstructed image generated from a reconstructing process that does not use the normal time information. As a result, according to the present application example, it is possible to generate a reconstructed image in which artifacts have been reduced.

The reconstruction processing function 444 is configured to generate the first reconstructed image by performing a reconstructing process that uses the paths according to the embodiment. Further, the reconstruction processing function 444 is configured to generate the second reconstructed image by performing a reconstructing process that does not use the time information. Because the reconstructing process related to generating the second reconstructed image corresponds to a known reconstructing process, explanations thereof will be omitted. In other words, the second reconstructed image is a reconstructed image in which artifacts such as a shower artifact and/or a streak artifact have been reduced, as compared to the first reconstructed image.

The image processing function 445 is configured to identify a region (hereinafter, "artifact region") having the occurrence of artifacts in the first reconstructed image. Because it is possible to apply a known technique to the identifying of the artifact region, explanations thereof will be omitted. From within the second reconstructed image, the image processing function 445 is configured to identify a partial image in the same position as the artifact region. Subsequently, the image processing function 445 is configured to replace the artifact region in the first reconstructed image with the partial image.

The photon counting X-ray CT apparatus 1 according to the second application example of the embodiment described above is configured to generate the first reconstructed image by performing the reconstructing process that uses the paths determined by the path determining function 443; to generate the second reconstructed image by performing the reconstructing process that does not use the time information; and to replace the image of the region (the artifact region) exhibiting the artifacts in the first reconstructed image, with the partial image in the same position as the artifact region in the second reconstructed image. As a result, because the artifact region in the first reconstructed image was replaced with the partial image in which the artifacts have been reduced, the photon counting X-ray CT apparatus 1 according to the second application example is able to generate a reconstructed image which has a high resolution and in which the artifacts have been reduced (inhibited). Because the other advantageous effects are the same as those of the embodiment, explanations thereof will be omitted.

When technical concept of the embodiment is realized as a reconstruction processing apparatus, the reconstruction processing apparatus includes the constituent elements of the console apparatus 40 illustrated in FIG. 1. In that situation, the processing circuitry 44 has a time information obtaining function. The processing circuitry 44 realizing the time information obtaining function corresponds to a time information obtaining unit. The reconstruction processing apparatus includes: the time information obtaining unit configured to obtain the time information corresponding to the timing at which the photons included in the X-rays were detected; and a reconstruction processing unit configured to perform the reconstructing process that uses the X-ray paths corresponding to the photons on the basis of the time information. Because the procedure and advantageous effects of the reconstructing process performed by the reconstruction processing apparatus are the same as those of the embodiment, explanations thereof will be omitted.

When technical concept of the embodiment is realized as a photon counting information obtaining method, the photon counting information obtaining method includes: outputting the pulse corresponding to the photons included in the X-rays; and obtaining the time information corresponding to the timing at which the photons were detected, on a basis of the pulse. Because the procedure and advantageous effects of the reconstructing process performed by the photon counting information obtaining method are the same as those of the embodiment, explanations thereof will be omitted.

When technical concept of the embodiment is realized as a reconstruction processing method, the reconstruction processing method includes: obtaining the time information corresponding to the timing at which the photons included in the X-rays were detected; and performing the reconstructing process that uses the X-ray paths corresponding to the photons, on the basis of the time information. Because the procedure and advantageous effects of the reconstructing process performed by implementing the reconstruction processing method are the same as those of the embodiment, explanations thereof will be omitted.

When technical concept of the embodiment is realized as a photon counting information obtaining program, the photon counting information obtaining program causes a computer to realize: outputting the pulse corresponding to the photons, in accordance with the detection of the photons included in the X-rays; and obtaining the time information corresponding to the timing at which the photons were detected, on the basis of the pulse. Further, when technical concept of the embodiment is realized as a reconstruction processing program, the reconstruction processing program causes a computer to realize: obtaining the time information corresponding to the timing at which the photons included in the X-rays were detected; and performing the reconstructing process that uses the X-ray paths corresponding to the photons, on the basis of the time information.

For example, it is also possible to realize the reconstructing process by installing the photon counting information obtaining program or the reconstruction program in a computer of a server apparatus (a processing apparatus) or the like connected to a photon counting X-ray CT apparatus and loading one of those programs into a memory. In that situation, the program capable of causing a computer to implement the method may be distributed as being stored in a storage medium such as a magnetic disk (e.g., a hard disk), an optical disc (e.g., a CD-ROM or a DVD), or a semiconductor memory. Because the processing procedure and advantageous effects of the photon counting information obtaining program and the reconstruction processing program are the same as those of the embodiment, explanations thereof will be omitted.

According to at least one aspect of the embodiments described above, it is possible, regarding the reconstruction of the image related to the photons included in the X-rays, to obtain the time information that makes it possible to enhance the spatial resolution of the image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photon counting X-ray computed tomography apparatus, comprising:

a photon counting detector configured to output a pulse corresponding to photons included in an X-ray, the photon counting detector including a plurality of detecting elements;

a time digital converter configured to obtain time information corresponding to a time at which the photons were detected, based on the pulse; and processing circuitry configured to identify a detecting element, of the plurality of detecting elements, related to the detection of the photons, based on the time information, identify a location of an X-ray tube focal point for a view related to the identified detecting element, based on the time information, determine a path of the X-ray at the time of the detection of the photons in the time information by connecting the identified detecting element to the identified location of the X-ray tube focal point, and perform a reconstructing process by using the determined path of the X-ray.

2. The photon counting X-ray computed tomography apparatus according to claim 1, wherein, as the reconstructing process, the processing circuitry is further configured to perform a successive approximation reconstruction based on forward projection and backward projection using the path.

3. The photon counting X-ray computed tomography apparatus according to claim 1, wherein the processing circuitry is further configured to:

use a backprojection method for the reconstructing process;

shift, prior to implementing the backprojection method, a reconstruction mathematical function in accordance with a position of each of the plurality of detecting elements; and perform the backprojection using the path on the shifted reconstruction mathematical function.

4. The photon counting X-ray computed tomography apparatus according to claim 1, wherein the processing circuitry is further configured to:

integrate pulse quantity values indicating how many pulses including the pulse were output from each of the plurality of detecting elements over a prescribed time period, by using the time information; and perform the reconstructing process based on a quantity value obtained by integrating the pulse quantity values and an average of a plurality of paths over the prescribed time period.

5. The photon counting X-ray computed tomography apparatus according to claim 1, wherein the processing circuitry is further configured to:

generate a first reconstructed image by performing the reconstructing process that uses the path;

generate a second reconstructed image by performing a reconstructing process that does not use the time information; and replace an image of a region exhibiting an artifact in the first reconstructed image, with a partial image in a same position as a region in the second reconstructed image.

6. The photon counting X-ray computed tomography apparatus according to claim 1, further comprising an X-ray tube configured to generate the X-ray at an X-ray tube focal point, wherein the processing circuitry is further configured to when the X-ray is generated at the X-ray tube focal point and the photons of the X-ray are detected by the detecting element of the plurality of detecting elements of the photon counting detector, determine a straight line connecting the X-ray tube focal point and the first detecting element as the path of the X-ray corresponding to the detection of the photons.

7. A reconstruction processing apparatus, comprising:

a time digital converter configured to obtain time information corresponding to a time at which photons included in an X-ray were detected by a photon counting detector that includes a plurality of detecting elements; and processing circuitry configured to identify a detecting element, of the plurality of detecting elements, related to the detection of the photons, based on the time information, identify a location of an X-ray tube focal point for a view related to the identified detecting element, based on the time information, determine a path of the X-ray at the time of the detection of the photons in the time information by connecting the identified detecting element to the identified location of the X-ray tube focal point, and based on the time information, perform a reconstructing process that uses the determined path of the X-ray, the path corresponding to the photons.

8. A non-transitory computer-readable storage medium storing therein a photon counting information obtaining program configured to cause a computer to perform:

outputting a pulse corresponding to photons, in accordance with detection, by a photon counting detector that includes a plurality of detecting elements, of the photons included in an X-ray;

obtaining time information corresponding to a time at which the photons were detected, based on the pulse, identifying a detecting element of the plurality of detecting elements, related to the detection of the photons, based on the time information, identifying a location of an X-ray tube focal point for a view related to the identified detecting element, based on the time information, determining a path of the X-ray at the time of the detection of the photons in the time information by connecting the identified detecting element to the identified location of the X-ray tube focal point, and performing a reconstructing process by using the determined path of the X-ray.

* * * * *